United States Patent
Wilks, Jr. et al.

(10) Patent No.: US 6,420,708 B2
(45) Date of Patent: Jul. 16, 2002

(54) SPECTROSCOPY ANALYZER USING A DETECTOR ARRAY

(75) Inventors: Paul A. Wilks, Jr., Darien; Kenneth R. Mateer, New Milford, both of CT (US)

(73) Assignee: Wilks Enterprise, Inc., South Norwalk, CT (US)

( * ) Notice: Subject to any disclaimer, the term of this patent is extended or adjusted under 35 U.S.C. 154(b) by 0 days.

(21) Appl. No.: 09/790,755

(22) Filed: Feb. 22, 2001

Related U.S. Application Data (60) Provisional application No. 60/188,510, filed on Mar. 10, 2000.

(51) Int. Cl.[7] .......................... G01N 21/27; G01N 21/35
(52) U.S. Cl. ......................... 250/339.07; 250/339.11; 250/339.13; 250/343; 356/300; 356/419
(58) Field of Search ............................ 356/300, 326, 356/328, 419; 250/339.07, 339.02, 339.11, 339.12, 339.13, 343

(56) References Cited

U.S. PATENT DOCUMENTS

| | | | |
|---|---|---|---|
| 4,730,882 A | 3/1988 | Messerschmidt | 385/146 |
| 4,975,581 A | 12/1990 | Robinson et al. | 250/339.11 |
| 5,159,199 A | 10/1992 | LaBaw | 250/339.02 |
| 5,166,755 A | 11/1992 | Gat | 356/419 |
| 5,483,335 A | 1/1996 | Tobias | 356/310 |
| 5,731,581 A | 3/1998 | Fischer et al. | 250/339.13 |
| 5,920,069 A | 7/1999 | Fischer et al. | 250/339.13 |

OTHER PUBLICATIONS

"Infrared in the Real World—How It Will Evolve in the New Millennum" by Paul Wilks, Spectroscopy, Dec. 1999, pps. 12–13.

"Hybrid Pyroelectric Linear Array With 128 Responsive Elements and Integrated CMOS Multiplexer" by Dias Angewandte Sensorik GmbH, May 1999, pps. 1–7, Pyroelectric Linear Array Z128–LT–20–2300.

*Primary Examiner*—F. L. Evans
(74) *Attorney, Agent, or Firm*—Ohlandt, Greeley, Ruggiero & Perle, L.L.P.

(57) ABSTRACT

An apparatus for analyzing a spectrum includes an elongated source of light, a device for producing a spectrum of the light, a sample stage, and an array of photosensitive elements for detecting the spectrum and providing an output representative of an intensity of the spectrum as a function of wavelength. The sample stage is interposed between the elongated source and the spectrum-producing device. The light propagates along a length of the sample stage from the elongated source to the spectrum-producing device. The elongated source has a length greater than or equal to a length of the array.

22 Claims, 5 Drawing Sheets

SPECTROSCOPY ANALYZER USING A DETECTOR ARRAY

CROSS REFERENCE TO RELATED APPLICATION

The present application is claiming priority of U.S. Provisional Patent Application Ser. No. 60/188,510, filed on Mar. 10, 2000.

BACKGROUND OF THE INVENTION

1. Field of the Invention

The present invention relates to spectroscopy, and more particularly to a spectroscopy analyzer using a detector array without requiring focusing optics, and having no optical path exposed to the atmosphere.

2. Description of the Prior Art

Several structures for multiple internal reflectance crystals are known in the art. For example, radiant energy, such as infrared (IR) energy, may enter a crystal through a first beveled face so as to reflect off a first side. The energy reflects between the first side and a second side down the length of the crystal by the physical phenomenon of total internal reflection. A sample that is placed against either the first or second side of the crystal selectively absorbs different frequencies of energy. The energy that is not absorbed exits the crystal through a second beveled face to a detector that measures the distribution of energy absorbed by the sample so as to obtain its spectrum.

Attenuated total reflection (ATR) is a technique of analyzing a sample material using infrared reflection. ATR allows an infrared measurement to be made in the midinfrared region over a very short optical path. The depth to which incident energy penetrates a sample depends on the refractive index of the sample and the multiple reflectance crystal, as well as the angle of incidence at which the energy reflects off of the side of the crystal that is in contact with the sample. Changing the angle at which energy enters the crystal, i.e., the entrance angle, may change the angle of incidence. A multiple internal reflectance crystal, however, introduces chromatic aberration into the resulting distribution of energy if the incident energy is not normal to the surface of an entrance face of the crystal.

U.S. Pat. No. 4,730,882 to Messerschmidt, entitled "Multiple Internal Reflectance Spectroscopy System", describes a design where any one of several multiple internal reflectance crystals, having different angles of incidence, can be positioned at a location that is remote from a source and receiver of radiant energy without the need for a realignment of transfer optics. A multiple internal reflectance crystal in accordance with the Messerschmidt patent has a sample surface and a bottom surface and reflective beveled ends such that energy may enter normal to the bottom surface, reflect off one beveled end to the bottom surface, from the bottom surface to the top surface, down the length of the crystal, and exit the crystal normal to the bottom surface by reflecting off of another beveled end.

A typical infrared spectrometer consists of a source of infrared radiation, a sample chamber where an exchange of energy takes place between the radiation and the sample, a means of dispersing the infrared radiation, i.e., a dispersing means such as a prism, a grating or an interferometer, and a detector that measures the energy level from the dispersing means. When the dispersing means is a prism or a grating, the dispersed radiation is scanned across a slit from whence it is focused on a detector. The spectrometer also includes focusing optics, such as a series of mirrors, some of which are aspheric, to focus light energy from the source onto the entrance face of the sample chamber, and from the sample chamber to the dispersing means and from thence through the exit slit to the detector. The total optical path may be a meter or more. Because of the long optical path, the spectrometer must be purged with a nitrogen gas or evacuated to eliminate absorption from atmospheric gasses such as $CO_2$ and water.

Dispersion shifts occur with temperature change for all three dispersion methods, i.e., prism, grating and interferometer. Accordingly, the spectrometer must be maintained at a constant temperature.

A radiation detector can be a detector array, which consists of a number of detector elements located adjacent to each other. A grating focuses a slit image in the form of a dispersed band to illuminate the array with dispersed infrared radiation. However, such a design may involve several aspheric mirrors and an optical path of significant length. Temperature changes may also cause the dispersed band to move across the array, thus changing the wavelength distribution on the detector elements.

There is a need for a spectrometer that does not require focusing optics.

There is also a need for such a spectrometer that minimizes the length of the optical path.

There is also a need for such a spectrometer, the operation of which is not susceptible to a temperature variation.

SUMMARY OF THE INVENTION

In accordance with the present invention, an apparatus is provided for analyzing a spectrum. The apparatus includes an elongated source of light, a device for producing a spectrum of the light, a sample stage, and an array of photosensitive elements for detecting the spectrum and providing an output representative of an intensity of the spectrum as a function of wavelength. The sample stage is interposed between the elongated source and the spectrum-producing device. The light propagates along a length of the sample stage from the elongated source to the spectrum-producing device and thereafter to the array. The elongated source has a length greater than or equal to a length of the ar

DETAILED DESCRIPTION OF THE INVENTION

The present invention is directed toward a spectroscopy analyzer using a detector array without requiring focusing optics. An elongated source of radiation is mounted in near contact with one end of a sample stage, such as an ATR crystal or a rectangular light pipe, and an assembly including a linear variable filter (LVF) and the detector array is mounted in near contact with another end of the sample stage.

A linear variable filter is a device for dispersing infrared radiation. It is an optical element that passes radiation from an entrance face to an exit face. The wavelength of the radiation from the exit face varies along the length of the exit face.

When using an ATR crystal for the sample stage, the crystal is as wide as the length of the array, typically about 15 millimeters. The crystal functions as an optical fiber, funneling all of the radiation that strikes its internal parallel surfaces at greater than the critical angle from the source end where the radiation enters, to the detector end where the radiation exits.

Figure 1:
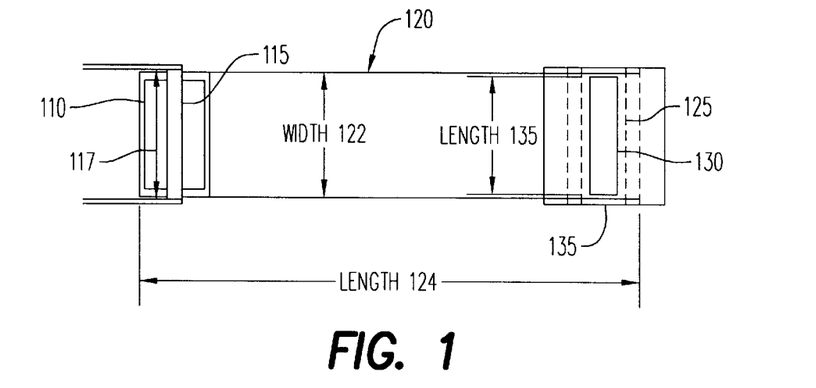
FIG. 1 is a top plan view of an apparatus for analyzing a spectrum in accordance with the present invention.

FIG. 1 shows an apparatus for analyzing a spectrum in accordance with the present invention. The apparatus includes a back reflector 110, an IR source 115, an ATR crystal 120, an LVF 125, a detector array 130 and an array case 135.

IR source 115 is an elongated source of light, preferably one that can be pulsed to produce an AC infrared signal. It has a length 117 greater than or equal to the length 132 of detector array 130. IR source 115 can be electronically pulsed or mechanically beam chopped. The light from IR source 115 is incident on ATR crystal 120.

Reflector 110 is an optional reflector for increasing the level of light incident on ATR crystal 120.

ATR crystal 120 is an internal reflectance crystal interposed between IR source 115 and LVF 125. It serves as a sample stage for supporting a sample material for attenuated total reflection analysis. The sample material can be a liquid, a semi-liquid, or a soft plastic. ATR crystal 120 has an entrance face adjacent to IR source 115, and an exit face adjacent to LVF 125. Preferably, the entrance face is less than or equal to 0.003 of an inch from IR source 115, and the exit face is less than or equal to 0.003 of an inch from LVF 125. The width 122 of ATR crystal 120 can be any convenient dimension that is greater than or equal to the length 135 of detector array 130. Light propagates along a length 124 of ATR crystal 120 from IR source 115 to LVF 125.

LVF 125 produces a spectrum of the light, preferably including wavelengths of between about 2.5 micrometers and 11 micrometers. The spectrum from LVF 125 is directed to detector array 130. The length and width of LVF 125 are the same as those of detector array 130.

Detector array 130 is an array of photosensitive elements for detecting said spectrum from LVF 125 and providing an output representative of an intensity of the spectrum as a function of wavelength. For example, if detector array 130 is composed of 128 elements, i.e., 128 pixels, it would provide an output representing 128 wavelengths.

Array case 135 provides a housing for LVF 125 and detector array 130. It also includes microelectronics (not shown) for processing the output of detector array 130.

Figure 2:
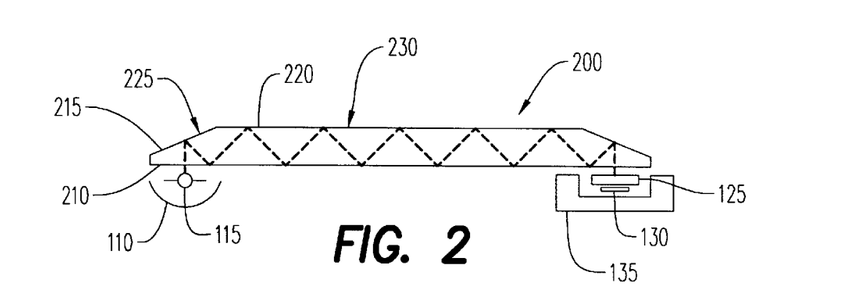
FIG. 2 is a side view of the apparatus shown in FIG. 1 having an ATR crystal of a first design.

FIG. 2 is a side view of the apparatus shown in FIG. 1 having an ATR crystal 200 of a first design. ATR crystal 200 includes a first side 210, a beveled edge 215 and a second side 220. Beveled edge 215 is oriented at an acute angle with respect to first side 210. Light from IR source 115 enters through first side 210 and travels from first side 210 to beveled edge 215, from beveled edge 215 to first side 210, and from first side 210 to second side 220. The exterior of beveled edge 225 is aluminized, and second side 220 also serves as a sample surface 230 for holding a sample of material for analysis. The light propagates along a length of ATR crystal 200 from IR source 115 to LVF 125.

Figure 3:
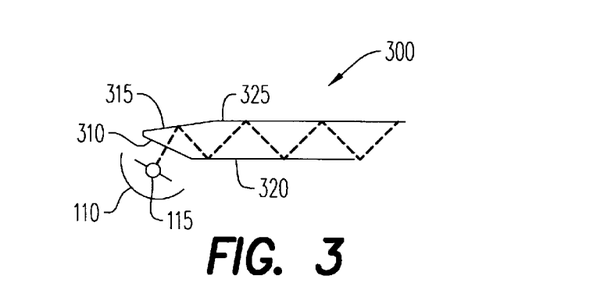
FIG. 3 is a partial side view of an ATR crystal of a second design for use in the apparatus shown in FIG. 1.

FIG. 3 is a partial side view of an ATR crystal 300 of a second design for use in the apparatus shown in FIG. 1. ATR crystal 300 has a first side 320, a second side 325, a first beveled edge 310 oriented at an obtuse angle with respect to first side 320, and a second beveled edge 315 oriented at an obtuse angle with respect to second side 325. Light from IR source 115 enters through first beveled edge 310 and travels from first beveled edge 310 to second beveled edge 315, from second beveled edge 315 to first side 320, and from first side 320 to second side 325. The light propagates along a length of ATR crystal 300 from IR source 115 to LVF 125 (shown in FIG. 1).

Figure 4:
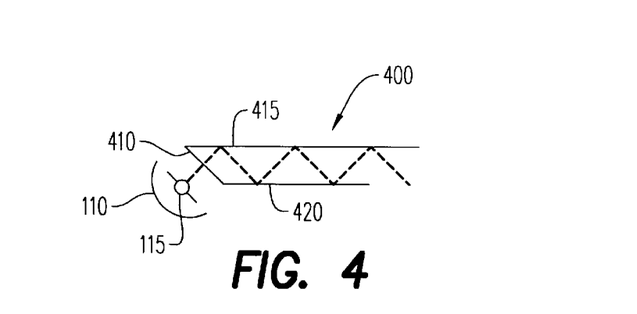
FIG. 4 is a partial side view of an ATR crystal of a third design for use in the apparatus shown in FIG. 1.

FIG. 4 is a partial side view of an ATR crystal 400 of a third design for use in the apparatus shown in FIG. 1. ATR crystal 400 has a first side 420, a second side 415 and a beveled edge 410 oriented at an obtuse angle with respect to first side 420. Light from IR source 115 enters through beveled edge 410 and travels from beveled edge 410 to second side 415, and from second side 415 to first side 420. The light propagates along a length of ATR crystal 400 from IR source 115 to LVF 125 (shown in FIG. 1).

Figure 5A:
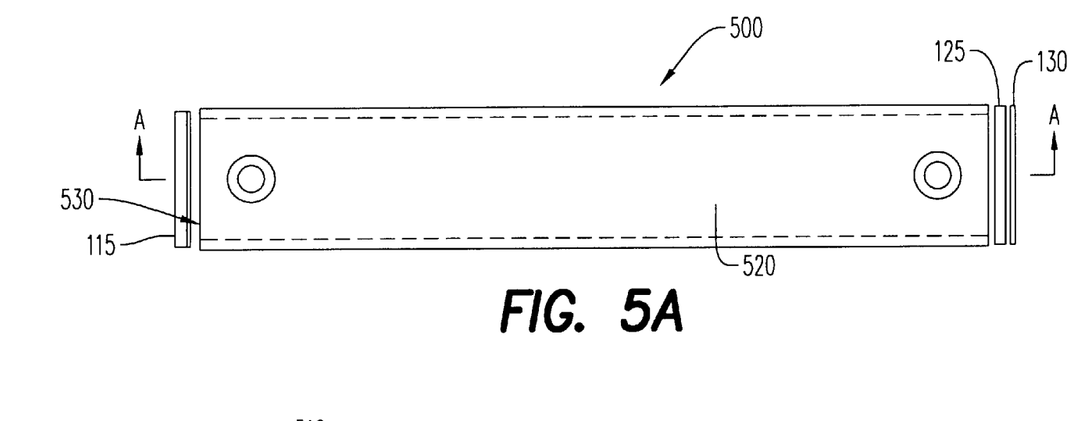
FIG. 5A is a top plan view of a rectangular light pipe.
Figure 5B:
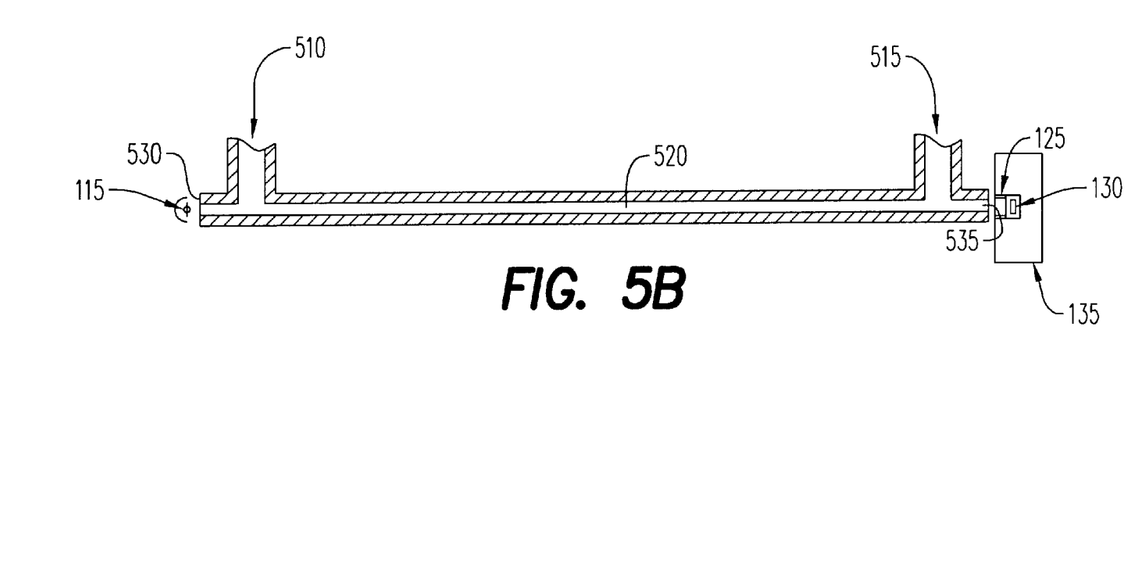
FIG. 5B is a vertical section taken along line A—A of the device shown in FIG. 5A.
Figure 5C:
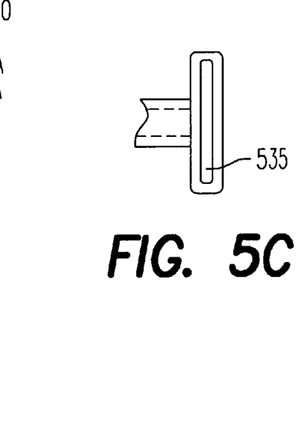
FIG. 5C is an end view of the device shown in FIG. 5A.

FIGS. 5A through 5C show three views of a rectangular light pipe 500, which can be used as a sample stage in the apparatus of FIG. 1, in place of ATR crystal 120 (shown in FIG. 1). Light pipe 500 includes a gas input port 510, a gas output port 515, a chamber 520, an entrance face 530 and an exit face 535.

Light pipe 500 can hold a sample gas for analysis by means of transmission. The sample gas is introduced into chamber 520 via gas input port 510. Chamber 520 has an internal surface with a reflective coating made of a material such as gold, silver, or aluminum, or a combination of such materials. The cross section of chamber 520 is approximately the same size as, or slightly greater than, that of detector array 130. Light from IR source 115 enters through entrance face 530 and travels through the sample gas in chamber 520 to exit face 535, and thereafter to LVF 125.

Figure 6:
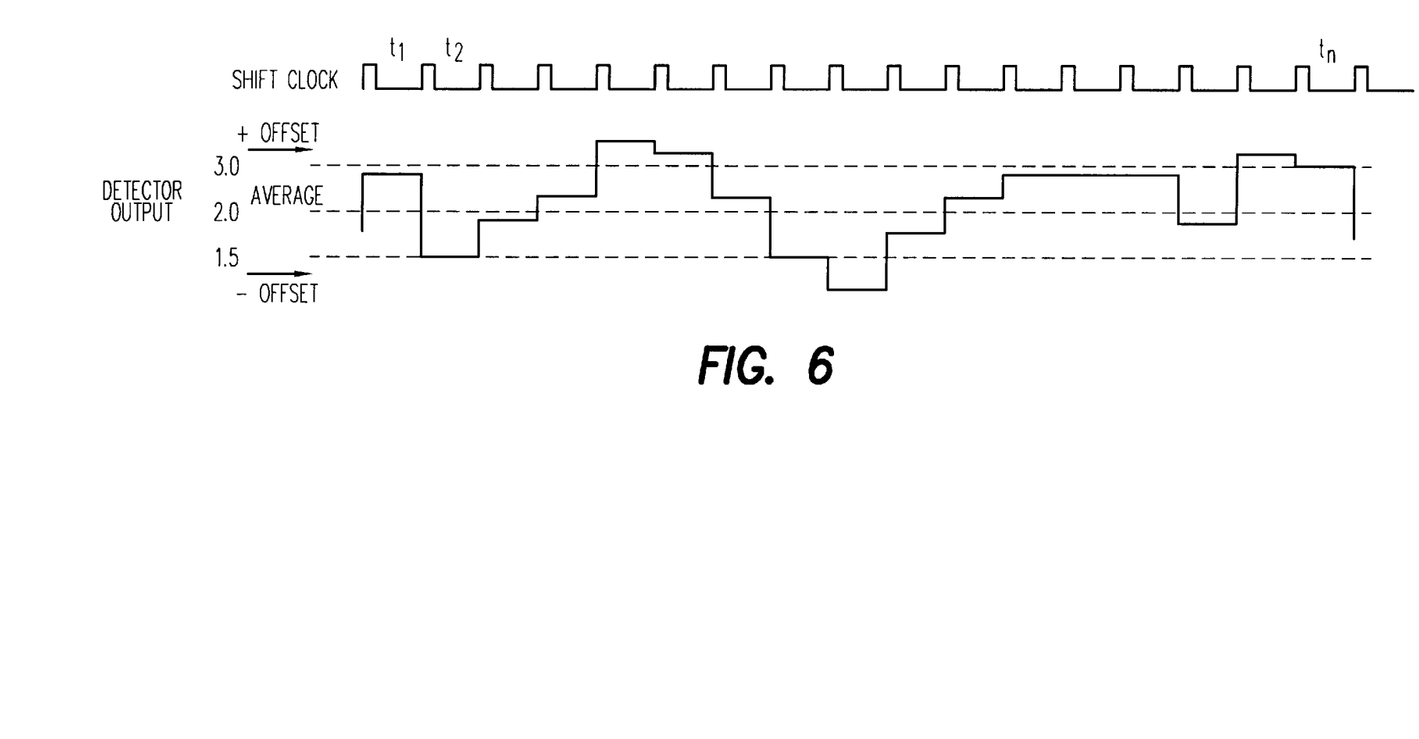
FIG. 6 is a timing diagram of an output of a detector array.

FIG. 6 is a timing diagram of an output of a detector array of a spectrometer, and more particularly, an output of a detector array when no sample has yet been introduced to the sample stage of the spectrometer, that is, under ambient conditions. FIG. 6 also shows a shift clock.

The output of the detector array includes a plurality of signals, each of which corresponds to a portion of the spectrum. Each shift clock interval, $t_1, t_2 \ldots t_N$, coincides with an output from a different array element. For example, the output at $t_1$ comes from array element 1, the output at $t_2$ comes from array element 2, and the output at $t_N$ comes from array element N.

Ideally, an array element produces no ambient signal. However, in a practical environment the array elements may output ambient signal levels as shown in FIG. 6. The ambient signal levels range between a maximum negative offset and a maximum positive offset. There is also an average ambient signal level. For purposes of example, assume that $element_2$ produces an ambient signal level of 1.5 volts, and $element_N$ produces an ambient signal level of 3.0 volts. Assume also that the average ambient signal level is 2.0 volts.

Signal$_2$=1.5 volts

Signal$_N$=3.0 volts

Average=2.0 volts

To facilitate processing of the detector array output during analysis of a sample, these ambient signal levels are nulled. That is, a calibration procedure is executed to counteract the ambient signal levels so that in the absence of a sample, a data stream representing the output of the detector array will be a continuous, static value.

Figure 7:
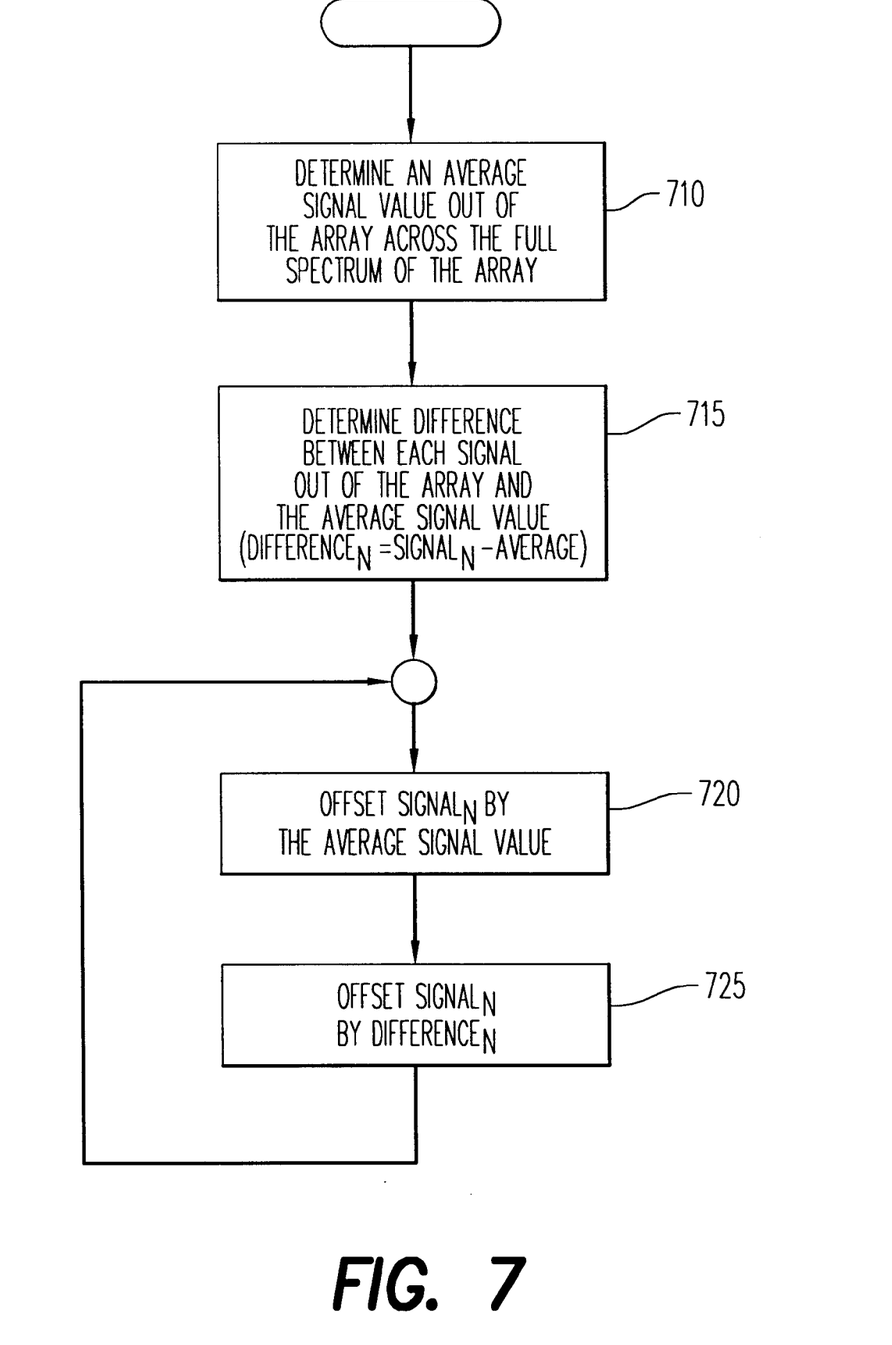
FIG. 7 is a flowchart of a method for nulling the output of a detector array in accordance with the present invention.

FIG. 7 is a flowchart of a method for nulling the output of a detector array in accordance with the present invention. The method begins with step 710.

In step 710, the method determines an average signal value out of the array across the full spectrum of the array. That is, the method determines the average of the outputs from all of the array elements. As stated above, for purposes of example, the average signal level is assumed to be 2.0 volts. The method then advances to step 715.

In step 715, the method determines a difference between each signal out of the array and the average signal value that was determined in step 710. For array signal element$_2$ and element$_N$:

Difference$_2$=Signal$_2$–Average

Difference$_2$=1.5 volts–2.0 volts

Difference$_2$=–0.5 volts

Difference$_N$=Signal$_N$–Average

Difference$_N$=3.0 volts–2.0 volts

Difference$_N$=1.0 volts

The difference is determined for each element of the detector array. The method then advances to step 720.

In step 720, the method offsets an output of an array element by the average signal level that was determined in step 710. The objective is to adjust the average signal level to a resultant of 0 volts. For example, given an average signal level of 2.0 volts, the method introduces an offset of –2.0 volts. That is:

Average Offset$_2$=–2.0 volts

Average Offset$_N$=–2.0 volts

The method then advances to step 725.

In step 725, the method offsets an output of an array element by the difference that was determined in step 715 for the element. For example, for element$_2$ and element$_N$:

Difference$_2$=–0.5 volts

Difference$_N$=1.0 volts therefore,

Difference Offset$_2$=0.5 volts

Difference Offset$_N$=–1.0 volts

In this example, for element$_2$ and element$_N$, the net offset from steps 720 and 725 yields:

Net Offset$_2$=Average Offset$_2$+Difference Offset$_2$

Net Offset$_2$=–2.0 volts+0.5 volts

Net Offset$_2$=–1.5 volts

Net Offset$_N$=Average Offset$_N$+Difference Offset$_N$

Net Offset$_N$=–2.0 volts–1.0 volts

Net Offset$_N$=–3.0 volts

Accordingly, the net result for element$_2$ and element$_N$ is:

Net Result$_2$=Signal$_2$+Net Offset$_2$

Net Result$_2$=1.5 volts–1.5 volts

Net Result$_2$=0 volts

Net Result$_N$=Signal$_N$+Net Offset$_N$

Net Result$_N$=3.0 volts–3.0 volts

Net Result$_N$=0 volts

The method then loops back to step 720. Steps 720 and 725 form a processing loop in which one element is processed for each pass through the loop. In this manner, the ambient output of each of the array elements will be nulled.

Thereafter, during an analysis of a sample, the ambient signal out of each element is actively nulled. After nulling, any remaining signal from an array element is attributed to the presence of the sample. This remaining signal is free of an interfering contribution of an ambient signal.

Figure 8:
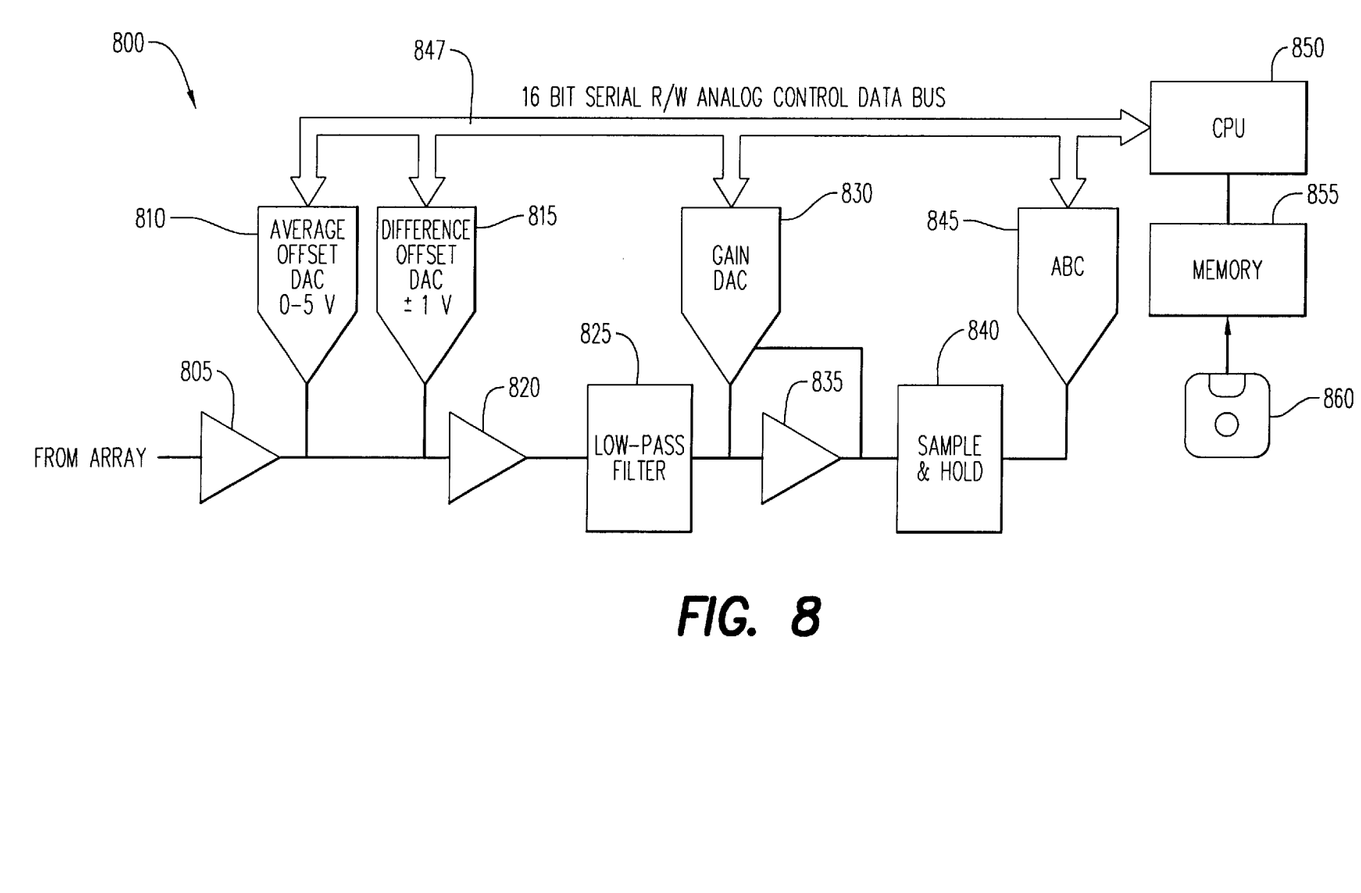
FIG. 8 is a block diagram of a circuit for processing the output of a detector array in accordance with the present invention.

FIG. 8 is a block diagram of a circuit 800 for processing the output of a detector array in accordance with the present invention. Circuit 800 includes amplifiers 805, 820 and 835, average offset digital-to-analog converter (DAC) 810, difference offset DAC 815, low pass filter 825, gain DAC 830, sample and hold 840, analog to digital converter (ADC) 845, central processing unit (CPU) 850 and memory 855.

Circuit 800 is particularly suited for processing the output of a detector array such detector array 130, shown in FIG. 1. The detector array output includes a plurality of signals, each of which corresponds to a portion of the spectrum. Circuit 800 is capable of nulling the output of the detector array as described above in the context of FIGS. 6 and 7.

A bus 847 interconnects, and provides a path for data and control signals between, CPU 850, average offset DAC 810, difference offset DAC 815, gain DAC 830 and ADC 845. That is, via bus 847, CPU 850 sends commands and data to average offset DAC 810, difference offset DAC 815, gain DAC 830, and CPU 850 receives data from ADC 845.

Amplifier 805 receives the output from the detector array. In turn, it provides an output that is coupled to an input of amplifier 820.

Average offset DAC 810 receives, from CPU 850, a digital representation of an average offset value for an element of the detector array. It performs an analog to digital conversion of the value and provides an analog output that is coupled to an input of amplifier 820.

Difference offset DAC 815 receives, from CPU 850, a digital representation of a difference offset value for an element of the detector array. It performs an analog to digital conversion of the value and provides an analog output that is coupled to the input of amplifier 820.

Amplifier 820 receives the output of amplifier 805, and it also receives an average offset signal from average offset DAC 810, and a difference offset signal from difference offset DAC 815. Accordingly, amplifier 820 combines an output from an array element, an average offset and a difference offset for the element, and produces a resultant output. Collectively, average offset DAC 810, difference offset DAC 815, under the control of CPU 850, and amplifier 820 provide a function analogous to that described in FIG. 7, steps 720 and 725. The output of amplifier 820 is coupled to an input of low pass filter 825.

Low pass filter 825 receives the output from amplifier 820. It is an active low pass analog filter that attenuates random noise level signals that may exist in the analog data stream from the detector array. The output of low pass filter 835 is coupled to an input of amplifier 835.

Amplifier 835 receives the output from low pass filter 825, and an output from gain DAC 830. Gain DAC 830 is a digitally controlled potentiometer. Amplifier 835, in cooperation with gain DAC 830, further amplify the output received from low pass filter 825. The output of amplifier 835 is coupled to an input of sample and hold 840.

Sample and hold 840, receives the output from amplifier 835 and, in turn, provides an output that is coupled to an input of ADC 845. Sample and hold 840 is an analog voltage storage device that is used to hold an analog voltage signal from amplifier 835 until ADC 845 completes its analog to digital conversion cycle.

ADC 845 receives the output from sample and hold 840, performs an analog to digital conversion, and provides an output to CPU 850 via bus 847.

CPU 850 receives the output from ADC 845. Memory 855 contains data and instructions for execution by CPU 850. By executing instructions obtained from memory 855, CPU 850 determines an average signal value out of the array across the full spectrum, and for each element of the array it determines a difference between a signal out of the element and the average signal value. As stated above, CPU 850 controls the nulling of the output of the array by sending the average signal value to average offset DAC 810, and sending the difference offset value to difference offset DAC 815.

CPU 850 also analyzes the output of the array, received from ADC 845, to quantify the intensity of the spectrum as a function of wavelength. More particularly, CPU 850 analyzes the signal from each element of the detector array after a sample has been applied to the sample stage. These signals are indicative of the molecular characteristics of the sample.

Circuit 800 can be implemented in hardware with discrete circuitry or firmware. Alternatively, it can be implemented in software for execution by a general-purpose processor or a digital signal processor. While the procedures required to execute the invention hereof are indicated as already loaded into memory 855, they may be configured on a storage media, such as data memory 860 for subsequent loading into memory 855.

A spectrometer constructed in accordance with the teachings of the present invention offers several advantages over the prior art. The present invention provides for a simple, low cost spectrometer that does not require expensive optical components. Because all components are in a common thermal environment, there are no optical paths that can be distorted by temperature variations. Likewise, there is no optical path where components in the atmosphere can cause interference. The present invention also offers greater sensitivity because it includes a sample stage of greater area than that of prior art systems, thus permitting more interaction between a sample and the IR radiation.

Those skilled in the art, having the benefit of the teachings of the present invention may impart numerous modifications thereto. Such modifications are to be construed as lying within the scope of the present invention, as defined by the appended claims.

What is claimed is:

1. An apparatus for analyzing a spectrum, comprising:
an elongated source of light;
means for producing a spectrum of said light;
a sample stage, interposed between said elongated source and said producing means, wherein said light propagates along a length of said sample stage from said elongated source to said producing means; and
an array of photosensitive elements, for detecting said spectrum and providing an output representative of an intensity of said spectrum as a function of wavelength,
wherein said elongated source has a length greater than or equal to a length of said array.

2. The apparatus of claim 1, wherein said sample stage has an entrance face adjacent to said elongated source.

3. The apparatus of claim 1, wherein said sample stage has an exit face adjacent to said producing means.

4. The apparatus of claim 1, wherein said sample stage has a width greater than or equal to a length of said array.

5. The apparatus of claim 1, wherein said sample stage is an internal reflectance crystal.

6. The apparatus of claim 5, wherein said crystal has a first side, a second side, and a beveled edge oriented at an acute angle with respect to said first side, and wherein said light enters through said first side and travels from said first side to said beveled edge, from said beveled edge to said first side, and from said first side to said second side.

7. The apparatus of claim 5, wherein said crystal has a first side, a second side, a first beveled edge oriented at an obtuse angle with respect to said first side, and a second beveled edge oriented at an obtuse angle with respect to said second side, and wherein said light enters through said first beveled edge and travels from said first beveled edge to said second beveled edge, from said second beveled edge to said first side, and from said first side to said second side.

8. The apparatus of claim 5, wherein said crystal has a first side, a second side and a beveled edge oriented at an obtuse angle with respect to said first side, and wherein said light enters through said beveled edge and travels from said beveled edge to said second side, and from said second side to said first side.

9. The apparatus of claim 5, wherein said crystal has a surface for supporting a sample material for attenuated total reflection analysis.

10. The apparatus of claim 1, wherein said sample stage is a rectangular light pipe.

11. The apparatus of claim 10, wherein said pipe holds a sample gas for analysis by means of transmission.

12. The apparatus of claim 10, wherein said pipe has an internal surface with a reflective coating.

13. The apparatus of claim 12, wherein said reflective coating is selected from the group consisting of gold, silver and aluminum, and mixtures thereof.

14. The apparatus of claim 1, wherein said light is an AC infrared signal.

15. The apparatus of claim 1, wherein said elongated source is electronically pulsed.

16. The apparatus of claim 1, wherein said elongated source is mechanically beam chopped.

17. The apparatus of claim 1, wherein said spectrum includes wavelengths of between about 5.5 to 11 micrometers.

18. The apparatus of claim 1, wherein said spectrum includes wavelengths of between about 2.5 to 5 micrometers.

19. The apparatus of claim 1, wherein said producing means is a linear variable filter.

20. The apparatus of claim 1, wherein said output of said array includes a plurality of signals, each of said plurality of signals corresponding to a portion of said spectrum,
   wherein said plurality of signals have an average value, and
   wherein said apparatus further comprises:
      means for nulling said output of said array.

21. The apparatus of claim 20,
   wherein said output of said array includes a signal that is one of said plurality of signals, and
   wherein said nulling means comprises:
      means for offsetting said signal by said average value; and
      means for offsetting said signal by a difference of said signal and said average value.

22. The apparatus of claim 1, further comprising a processor for analyzing said output of said array to quantify said intensity as a function of wavelength.

* * * * *